United States Patent [19]
Hirayama et al.

[11] 3,948,915
[45] Apr. 6, 1976

[54] 2-HALOPYRIMIDINE DERIVATIVES AND A METHOD FOR THEIR PREPARATION
[75] Inventors: Tadamasa Hirayama; Masahiro Kamada; Hideaki Tsurumi, all of Tokyo, Japan
[73] Assignee: Daiichi Seiyaku, Co., Ltd., Tokyo, Japan
[22] Filed: July 8, 1974
[21] Appl. No.: 486,634

[52] U.S. Cl........ 260/256.4 C; 260/465 E; 260/999
[51] Int. Cl.²............... C07D 239/26; C07D 239/34
[58] Field of Search............................. 260/256.4 C

[56] References Cited
FOREIGN PATENTS OR APPLICATIONS
41-19808   11/1966   Japan.......................... 260/256.4 C OTHER PUBLICATIONS
Nitta et al., "Chemical Abstracts," Vol. 63, 1965, Col. 11556g.
Grigat et al., "Chemical Abstracts," Vol. 64, 1966, Col. 2086g.

Primary Examiner—Richard J. Gallagher
Assistant Examiner—James H. Turnipseed
Attorney, Agent, or Firm—Oblon, Fisher, Spivak, McClelland & Maier

[57] ABSTRACT
A process for preparing a 2-halopyrimidine derivative represented by the formula:

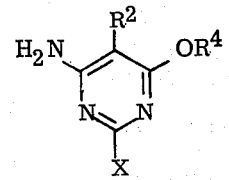

wherein $R^2$ represents a hydrogen atom, a halogen atom, a lower alkyl group, an aryl group, and an amino group and $R^4$ represents a lower alkyl group and X represents a halogen atom, which comprises reacting cyanoacetimidate derivative represented by the formula:

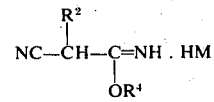

wherein $R^2$ and $R^4$ represent the same as above and M represents a mineral acid residue with cyanamide, to produce an N-cyanocyanoacetimidate

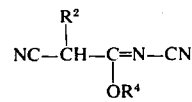

represented by the formula:
wherein $R^2$ and $R^4$ represent the same as above, and thereafter reacting said N-cyanocyanoacetimidate with a hydrogen halide.

5 Claims, No Drawings

2-HALOPYRIMIDINE DERIVATIVES AND A METHOD FOR THEIR PREPARATION

BACKGROUND OF THE INVENTION

1. Field of the Invention

This invention relates generally to 2-halopyrimidine derivatives represented by the general formula (I),

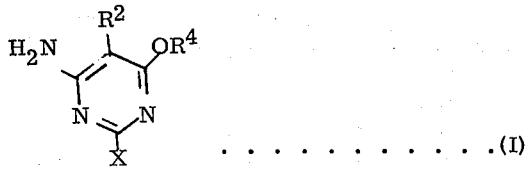

wherein $R^2$ represents hydrogen, halogen, particularly chlorine, bromine, iodine and fluorine, $C_1$-$C_6$ lower alkyl, aryl, particularly phenyl, $C_1$-$C_6$ alkyl substituted phenyl, halogen substituted phenyl or the like, or an amino group, particularly $NH_2$, $NR^5H$ or $NR_2^5$ wherein $R^5$ is similar to $R^2$ and $R^4$ represents a $C_1$-$C_6$ lower alkyl, and X represents a halogen, particularly chlorine, fluorine, bromine, and iodine, and further relates to novel intermediate compounds useful for their preparation. The compounds represented by the formula (I) are important for use in the preparation of sulfa drugs, purine bases or the like.

2. Description of the Prior Art

Heretofore, only one method has been known for the production of 2-halogeno-4-alkoxy-6-aminopyrimidine derivatives represented by the general formula (I). In that method, 6-amino-2,4-dichloro-pyrimidine derivatives are reacted with sodium alcoholate (refer to Chemical & Pharmaceutical Bulletin vol. 13, page 557 (1965) and Japanese Patent publication number 19804/1966). However, as described in those reports, the major product is 2-alkoxy-4-chloro-6-aminopyrimidine, although 4-alkoxy-2-chloro derivative is obtained as a by-product in a poor yield, because the reactivity of the halogen atom at the 2-position of the pyrimidine ring is far superior to the reactivity of the halogen atom at the 4-position of the pyrimidine ring. It is therefore chemically impossible to obtain 2-halogeno-4-alkoxy-6-aminopyrimidine derivatives as a main product by the prior art technique. Moreover, the prior art technique suffers certain other disadvantages. For one, it requires a procedure which is undesirable from a pollution point of view. For another, phosphorous acid salts are produced from the phosphorous oxychloride which amplifies the pollution difficulties. The prior art technique is therefore industrially not completely satisfactory.

SUMMARY OF THE INVENTION

Accordingly, it is one object of this invention to provide a process for producing (I) which avoids the difficulties as above described, yet which is capable of producing (I) in an economically attractive manner.

This and other objects of this invention, as will hereinafter become more readily appreciated by reference to the following description, by the method:

(wherein $R^2$, $R^4$ and X are the same as hereinbefore defined and M means a mineral acid residue, such as a halide, sulfonate, sulfate, sulfide, etc.

DETAILED DESCRIPTION OF THE PREFERRED EMBODIMENT

According to the present invention, pyrimidine bases represented by the formula (I) is prepared by condensing cyanoacetimidate derivatives represented by the formula (II) with cyanamide (III) to produce N-cyanocyanoacetimidate derivatives represented by the formula (IV), and by further cyclizing the resulting product (IV) in the presence of a hydrogen halide.

The reactants (II) used in this invention can be easily produced in good yields from malonitrile or a derivative thereof according to the S. M. McElvain method (J.Am.Chem.Soc. 71 40 (1949)). Cyanamide (III) is a commercially available compound. Heretofore, a method analogous to the first step of the present invention has been disclosed in (A) W. Lwowski, SYNTHESIS 263 (1970) and (B) K. R. Huffman et al, J.Org.Chem. 28, 1816, (1963).

N - cyanoimidate derivatives of the formula:

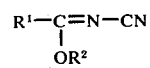

(wherein $R^1$ is an alkyl group, particularly $C_1$-$C_{10}$ or an aryl group, particularly phenyl, or lower alkyl phenyl, or halogen substituted phenyl, and $R^2$ is an alkyl group, particularly $C_1$-$C_{10}$) are produced by reacting alkyl- or arylimidate derivatives of the formula:

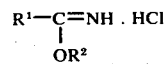

(wherein $R^1$ and $R^2$ mean the same as above) with cyanamide (A) in an aqueous solvent adjusted to pH 6.5–7.0 with $Na_2HPO_4$ or (B) in an alcoholic solvent. However, these reactions proceed only when the $R^1$ has no functional groups thereon such as a cyano, hydroxy or halogen group. The presence of functional groups on R completely alters the reaction (see page 1816 in the above reference (B)).

It would thus have been considered that N-cyano cyanoalkylimidates of formula (IV), which have a functional substituent could not be obtained by reacting the raw material (II) with cyanamide. Certainly, when the present inventors tried to react the raw material (II)

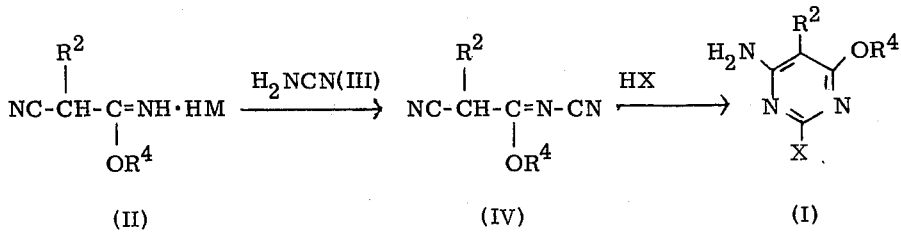

with cyanamide under the condition of (A) and (B) as described in the aforementioned reports, the desired compound of this invention (IV) could not be obtained. Further investigation, however, uncovered an unexpected fact.

If the alkyl group of the alkylimidate derivatives contains a substituent as shown in the formula (II), it is sufficient to react alkylimidate hydrogen halide derivatives with cyanamide in an inert solvent, to obtain the desired compound (IV). Accordingly, all the compounds represented by the formula (IV) are novel compounds. Suitable such solvents include the polyhalogenated hydrocarbons, such as chloroform, dichloroethylene trichloroethane, or carbon tetrachloride; aromatic hydrocarbons, such as benzene, toluene or xylene are desirable, however, ethers, ketones, esters or petroleum hydrocarbons can be used, and non-polar solvents can be used in general. Alcohols are specifically unsuited. In order to carry out this reaction more smoothly, it is desirable to add a silicate compound such as silica gel, natural or synthetic zeolite, a molecular sieve, a metal oxide such as alumina, zinc oxide, magnesium oxide or titanium oxide, or an inorganic salt, such as calcium carbonate, barium carbonate, calcium sulfate, barium sulfate, calcium chloride or barium chloride.

The reaction can be carried out at a temperature of 0°–60°C, and generally 15°–30°C is preferable. The product (IV) can be isolated from its reaction mixture. By-products and ammonium salts, such as ammonium chloride, and the silicate or inorganic additives can be filtered off. The reaction solvent is then removed by distillation to yield the compound (IV) in high purity.

Furthermore, the present invention provides a new method for producing pyrimidine base by cyclization. In order to produce pyrimidine base (I), the compound (IV) is dissolved in a suitable solvent and hydrogen halide is introduced into the solution, or the solution is mixed with a solvent containing hydrogen halide. By cyclization of compound (IV), two kinds of pyrimidine base can be produced. However, 2-halopyrimidine, which is the desired compound, can be obtained selectively by cyclizing compound (IV) in the presence of a Lewis acid such as boron trifluoride ethyl ether complex.

In the above reaction, any solvent which will not react with hydrogen halide or the compound (IV), can be used. Furthermore, any solvent which can dissolve a suitable amount of hydrogen halide is more desirable. Usually, ethers, such as ethyl or propyl ether; aromatic hydrocarbons, such as benzene, toluene or xylene; ketones such as acetone, methylethylketone or methylisobutylketone; polyhalogenated hydrocarbons, such as chloroform, dichloroethylene, trichloroethane or carbon tetrachloride, or a mixture thereof can be used.

The reaction temperature is not particularly critical. Usually the reaction will proceed easily at temperatures of 15°–30°C, but temperatures of 0°–60°C are satisfactory. Hydrogen halide can be used with one equivalent mole or more of compound (IV), but an excess amount, 3–6 times moles to the compound (IV) is preferable. The concentration of hydrogen halide in the solution is not particularly critical. For example, the reaction will proceed smoothly in a 20% ether solution of hydrogen halide or in a 1% ethylene dichloride of hydrogen halide.

Although the product (I) precipitates as its hydrogen halide salt from the reaction solution, it easily changes to free base by post-treating in aqueous solution. It can then be easily isolated in any conventional manner, such as by filtration.

As described above, the reaction (II) → (IV) → (I) provides a significant method to the synthetic chemistry and industrial field, because it not only enables the production of pyrimidine bases which had heretofore been difficult to synthesize, but also these reactions can be carried out under mild conditions. Isolation of the product is very easy, and it is not necessary to use a halogenating agent, which may cause pollution difficulties.

The compound (I) is expected to be utilized in a broad field, especially when a compound (I:$R^1$=$CH_3$, $R^2$=H, X=Cl) is made to react with sodium methylate or to be reductively dehalogenated by the usual manner, it can easily be conducted to 2,4-dimethoxy-6-aminopyrimidine or 4-methoxy-6-aminopyrimidine, respectively, which are important as sulfa drug bases.

Having generally described the invention, a more complete understanding can be obtained by reference to certain specific examples, which are included for purposes of illustration only and are not intended to be limiting unless otherwise specified.

EXAMPLE 1

2.97 g of methyl α-methylcyanoacetimidate hydrochloride and 1.26 g of cyanamide were suspended in 30 ml of benzene and made to react for 5 hours at 25°C. Then, ammonium chlordie precipitate was filtered off and then the filtrate was concentrated to dryness in vacuo and 2.38 g of methyl N-cyano-α-methycyanoacetimidate was obtained (yield 86.8%) mp 68.5°C. Analysis calculated for $C_6H_7N_3O$ (%) C 52.54, H 5.15, N 30.64, found C 52.57, H 5.14, N 30.62.

EXAMPLE 2

4.21 g of methyl α-phenylcyanoacetimidate hydrochloride and 1.26 g of cyanamide were mixed at room temperature and the mixture was made to react for 5 hours. Then, 50 ml of benzene was added to the reaciton mixture to extract the resulting product. The extracted solution was concentrated to dryness in vacuo and 3.06 g of methyl N-cyano-α-phenylcyanoacetimidate was obtained (yield 76.8%).

The structure of this compound was confirmed by NMR and IR.

EXAMPLE 3

2.97 g of ethyl cyanoacetimidate hydrochloride, 1.26 g of cyanamide and 5.0 g of alumina were suspended in 30 ml of benzene. Then this was treated with the same manner as in Example 1, and 2.29 g of ethyl N-cyanoacetimidate was obtained (yield 83.6%) mp 64.5°C. Analysis calculated for $C_6H_7N_3O$ (%) C 52.55, H 5.15, N 30.64, found C 52.47, H 5.12, N 30.38.

EXAMPLE 4

3.25 g of n-propyl cyanoacetimidate hydrochloride and 1.26 g of cyanamide were treated with the same manner as in Example 1 and 2.18 g of oily n-propyl N-cyanocyanoacetimidate was obtained (yield 72.1%). The structure of this compound was confirmed by IR and NMR. Analysis calculated for $C_7H_9N_3O$ C 55.62, H 6.00, N 27.80, found C 54.80, H 6.27, N 27.13.

EXAMPLE 5

3.25 g of isopropyl cyanoacetimidate hydrochloride and 1.26 g of cyanamide were treated with the same manner as in Example 1 and 2.07 g of isopropyl N-cyanocyanoacetimidate was obtained (yield 68.5%) mp 66.5°C. Analysis calculated for $C_7H_9N_3O$ (%) C 55.62, H 6.00, N 27.80, found C 55.41, H 5.91, N 27.66.

EXAMPLE 6

2.69 g of methyl cyanoacetimidate hydrochloride, 1.68 g of cyanamide and 5.0 g of molecular sieve (type 4A, 60 mesh through) were suspended in 30 ml of benzene and the suspension was made to react for 5 hours at 25°C under stirring. After reaction, insoluble materials were filtered off and then the filtrate was concentrated to dryness in vacuo to give 2.26 g of methyl N-cyanocyanoacetimidate (yield 91.2%) mp 45.5°C.

Analysis calculated for $C_5H_5N_3O$ (%) C 48.78, H 4.09, N 34.13, found C 48.61, H 4.12, N 33.98.

After 1.23 g of methyl N-cyanocyanoacetimidate obtained above was dissolved in 10 ml of a mixed solvent benzene-ether (1:2), 0.14 g of boron trifluoride ethylether complex was added to the solution and 10.7 g of a 20.5% ether solution of hydrogen chloride was added dropwise at 25°C to the solution. Then, the solution is made to react for 6 hours at the same temperature. After the reaction, the solvent is distilled off to give a residue. The residue is dissolved in 10 ml of water and the solution was neutralized with sodium bicarbonate solution to precipitate. Then, the precipitates were collected by filtration, washed with water and dried to give 1.48 g of 2-chloro-4-methoxy-6-aminopyrimidine (yield 92.5%) mp 186°C.

EXAMPLE 7

After 1.37 g of methyl N-cyano-α-methyl-cyanoacetimidate obtained with the same manner described in Example 1 was dissolved in 15 ml of a mixed solvent benzene-ether (1:2), 0.14 g of boron trifluoride ethylether complex was added to the solution and 1.1 g of hydrogen chloride was introduced by degrees for 2 hours at 25°C to the solution. Then, the solution was made to react for 3 hours at the same temperature. After the reaction, the solvent was distilled off to give a residue. The residue was dissolved in 10 ml of water and the solution was neutralized with sodium bicarbonate solution to precipitate. Then, the precipitates were collected by filtration, washed with water and dried to give 1.42 g of 2-chloro-4-methoxy-5-methyl-6-aminopyrimidine (yield 81.6%) mp 189°C.

Analysis calculated for $C_6H_8N_3O$ Cl (%) C 41.51, H 4.65, N 24.24, Cl 20.24, found C 41.54, H 4.95, N 23.77, Cl 20.66.

EXAMPLE 8

After 1.99 g of methyl N-cyanocyanoacetimidate obtained with the same manner in Example 2 was dissolved in 15 ml of ether, 6.6 g of a 16.7% ether solution of hydrogen chloride was added at 25°C to the solution. Then, the solution was made to react for 5 hours at the same temperature. The resulting solution was treated with the same manner as the latter half of Example 7 and 1.66 g of 2-chloro-4-methoxy-5-phenyl-6-aminopyrimidine is obtained (Yield 70.3%) mp 213°C.

Analysis calculated for $C_{11}H_{10}N_3OCl$ 235.675 (%) C 56.06, H 4.28, N 17.83, Cl 15.04, found C 56.04, H 4.31, N 17.71, Cl 15.67.

EXAMPLE 9

1.37 g of ethyl N-cyanocyanoacetimidate obtained with the same manner in Example 3 was treated with the same manner as in Example 7 and 1.49 g of 2-chloro-4-ethoxy-6-aminopyrimidine was obtained (yield 85.6%) mp 133°C analysis calculated for $C_6H_8N_3OCl$ (%) C 41.51, H 4.64, N 24.20, Cl 20.42, found C 41.69, H 4.67, N 24.34, Cl 20.63.

EXAMPLE 10

2.69 g of methyl cyanoacetimidate hydrochloride, 1.68 g of cyanamide and 5.0 g of molecularsieves (type 4A, 60 mesh) were suspended in 30 ml of benzene and the suspension was made to react for 5 hours at 25°C. After reaction, insoluble materials were filtered off and 30 ml of ether solution containing 0.28 g of boron trifluoride ethylester complex was added to the filtrate, then 2.9 g of gaseous hydrogen chloride was introduced into the mixture slowly at 20°–25°C. After the mixture was stirred for 6 hours at the same temperature, the solvent was distilled off to give a residue.

The residue was dissolved in 20 ml of water and the solution was neutralized with sodium bicarbonate solution to precipitate. Then, the precipitates were collected by filtration, washed with water and dried to give 2.59 g of 2-chloro-4-methoxy-6-aminopyrimidine (yield 81.1%) mp 186°C.

EXAMPLE 11

After 1.23 g of methyl N-cyanocyanoacetimidate was dissolved in 10 ml of glacial acetic acid, 10.7 g of a 20% ether solution of hydrogen chloride was added dropwise at 15°–25°C to the solution. Then, the solution was made to react for 6 hours at room temperature. After the reaction, the solvent was distilled off to give a residue. The residue was dissolved in 10 ml of water and the solution was neutralized with sodium bicarbonate solution to give precipitates. Then, the precipitates were collected by filtration, washed with water and dried to give 1.47 g of crude crystals. The crystals were recrystallized from diluted hydrochloric acid to give 1.33 g of 2-chloro-4-methoxy-6-aminopyrimidine (yield 83.1%), mp 186°–187°C.

Having now fully described the invention, it will be apparent to one of ordinary skill in the art that many changes and modifications can be made thereto without departing from the spirit or scope of the invention as set forth herein.

What is claimed as now and intended to be covered by Letters Patent is:

1. A process for preparing a 2-halopyrimidine compound represented by the formula:

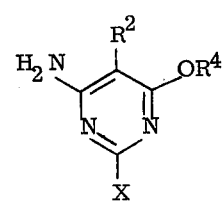

wherein $R^2$ represents hydrogen, halogen, $C_{1-6}$ lower alkyl, phenyl, $C_{1-6}$ alkyl or halo-substituted phenyl, or amino, and $R^4$ represents $C_{1-6}$ lower alkyl and X represents Cl, Br, F, or I, which comprises the steps of:
reacting a cyanoacetimidate compound represented by the formula:

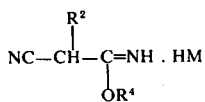 . HM wherein $R^2$ and $R^4$ represent the same as above, and M represents a mineral acid residue, with cyanamide, to produce an N-cyanocyanoacetimidate represented by the formula:

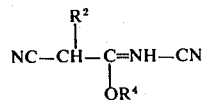

wherein $R^2$ and $R^4$ represent the same as above, and thereafter reacting said N-cyanocyanoacetimidate with HF, HCl, HBr, or HI.

2. A process for preparing a 2-halopyrimidine compound represented by the following general formula:

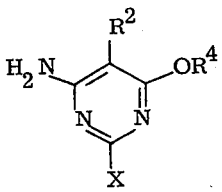

wherein $R^2$ represents hydrogen, halogen, $C_{1-6}$ lower alkyl, phenyl, $C_{1-6}$ alkyl or halo-substituted phenyl, or amino, and $R^4$ represents $C_{1-6}$ lower alkyl and X represents F, Cl, Br, or I, which comprises the steps of:
reacting an N-cyanocyanoacetimidate compound represented by the general formula:

wherein $R^2$ and $R^4$ are as defined above with HF, HCl, HBr, or HI.

3. A compound of the formula:

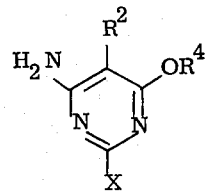

wherein $R^2$ represents halogen, $C_{1-6}$ lower alkyl, phenyl, $C_{1-6}$ alkyl or halo-substituted phenyl, or amino, and $R^4$ represents $C_{1-6}$ lower alkyl and X represents Cl, F, Br, or I.

4. The compound of claim 1, which is 2-chloro-4-methoxy-5-methyl-6-aminopyrimidine.

5. The compound of claim 1, which is 2-chloro-4-methoxy-5-phenyl-6-aminopyrimidine.

* * * * *